United States Patent [19]

Giordano et al.

[11] Patent Number: 5,097,059

[45] Date of Patent: Mar. 17, 1992

[54] RESOLUTION PROCESS OF INTERMEDIATES USEFUL FOR THE PREPARATION OF DILTIAZEM

[75] Inventors: Claudio Giordano, Monza; Dario Tentorio, Vigano'; Roberto Casagrande, Bresso; Placido Bertin, Battaglia Terme; Valeriano Merli, Occhiobello; Giorgio Sagramora, Padova, all of Italy

[73] Assignee: Zambon Group S.p.A., Vicenza, Italy

[21] Appl. No.: 557,808

[22] Filed: Jul. 26, 1990

[30] Foreign Application Priority Data

Jul. 27, 1989 [IT] Italy ................. 21338 A/89

[51] Int. Cl.$^5$ .................................. C07B 57/00
[52] U.S. Cl. ...................... 560/17; 540/491; 562/402; 562/431
[58] Field of Search .......... 560/17; 562/402; 540/491

[56] References Cited

U.S. PATENT DOCUMENTS 4,552,695 11/1985 Igarashi et al. ................. 540/491
4,908,469 3/1990 Martin .............................. 560/17
4,931,587 6/1990 Piselli ............................. 562/401

Primary Examiner—Jose G. Dees
Assistant Examiner—Vera C. Clarke
Attorney, Agent, or Firm—Stevens, Davis, Miller & Mosher

[57] ABSTRACT

A process of spontaneous resolution of compounds of formula

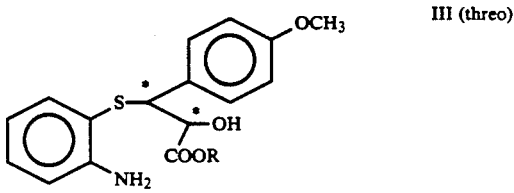

wherein R has the meanings reported in the description, is described.

The compounds of formula III are intermediates useful for the preparation of Diltiazem.

4 Claims, No Drawings

RESOLUTION PROCESS OF INTERMEDIATES USEFUL FOR THE PREPARATION OF DILTIAZEM

The present invention relates to a process for the optical resolution of intermediates useful for the preparation of Diltiazem and, more particularly, it relates to a process for the optical resolution of esters of threo-2-hydroxy-3-(2-aminophenylthio)-3-(4-methoxyphenyl)-propionic acid.

Diltiazem, (+)-(2S,3S)-3-acetoxy-5-[2-(dimethylamino)-ethyl]-2,3-dihydro-2-(4-methoxyphenyl)-1,5-benzothiazepin-4(5H)-one (Merck Index, X Ed., No. 3189, page 466) is a known drug with calcium-antagonist activity described in British specification No. 1,236,467 (Tanabe Seiyaku Co. Ltd.).

Several methods for the preparation of Diltiazem are known in literature such as, for example, the methods described in the above British specification No. 1,236,467 and in Japanese patent No. 71/8982 (Tanabe Seiyaku Co. Ltd.) (Chem. Abstrs. 75:36164u). Most of these methods substantially follow the below reported synthetic scheme.

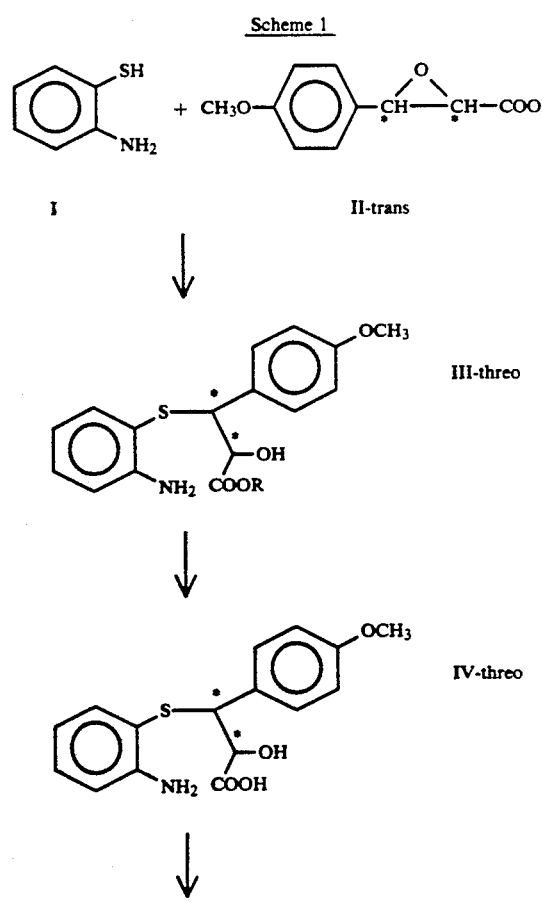

wherein R is a lower alkyl and the asterisks mark the asymmetric carbon atoms.

Each of these methods necessarily needs an optical resolution step, generally at the level of an intermediate of the synthesis, in order to separate the (2S,3S) enantiomer from the (2R,3) one.

In fact, the resolution of the intermediate of formula IV with optically active bases such as alpha-phenylethylamine, described in the European patent No. 98,892 (Tanabe Seiyaku Co. Ltd.), and L-lysine, described in the U.K. patent application No. 2,130,578 (Istituto Luso Farmaco), are known.

Nevertheless, the above reported methods need expensive resolving agents and their optional recycle requires long and cumbersome steps. To our knowledge, spontaneous resolution processes at the level of the intermediates for the preparation of Diltiazem have never been described in literature.

We have now surprisingly found that the intermediate of formula III may be conveniently resolved in the two enantiomers (2S,3S) and (2R,3R) by spontaneous resolution of the racemic mixture. This allows to avoid the use of resolving agents and the subsequent purifications which reduce the global yields of the process, besides increasing the expenses. Thus, object of the present invention is a process for the spontaneous resolution of threo-2-hydroxy-3-(2-aminophenylthio)-3-)4-methoxyphenyl)propionic acid lower esters, preferably the methyl ester, of formula III by crystallization of a mixture of the two enantiomers (2R,3R) and (2S,3S) wherein one prevails over the other, from supersaturated solutions of the intermediate of formula III in an inert polar solvent, or in a mixture of solvents at least one of which is polar, and wherein the racemic mixture is soluble.

Specific examples of suitable polar solvents are alcohols such as methanol and isopropanol, weak organic acids such as acetic acid, and dipolar aprotic solvents such as dimethylformamide. Small amounts of water are allowed too. Mixtures of isopropanol:acetic acid or toluene:dimethylformamide are preferably used.

Not suitable solvent for the process of the present invention are the acidic solvents with $pK_a$ lower than 4 or the solvents that interfere with the functions of the molecule of intermediate III. In the spontaneous resolution process object of the present invention a mixture of the enantiomers (2R,3R) and (2S,3S) of compound III wherein one of the two enantiomers slightly prevails over the other is employed as starting product.

This mixture may be artificially prepared by adding one of the enantiomers to the racemic mixture (generally the undesired enantiomer) or may result from preceding synthetic steps. The complete solubilization of the compound of formula III may be generally obtained at temperatures between 40° and 50° C. with a fairly high concentration even of 25-30% w/v. The solution is maintained under mild stirring, then is cooled to a temperature lower than 35° C., the preferred crystallization of the major enantiomer of the ester of formula III is seeded by adding a small amount of the same enantiomer.

The industrial application of the process object of the present invention is also possible because the solution stability allows to filter the precipitate at room temperature.

After filtration of the crystallized, an amount of the racemic mixture of the compound of formula III equal to the amount of the precipitated enantiomer is added to the mother liquors and it is heated up to complete dissolution.

If necessary the starting conditions are restored by adding racemic mixture and undesired enantiomer and if needed the solution volume is restored too.

The preceding steps are repeated by obtaining a new precipitate (the other enantiomer).

The starting conditions are restored by filtration of the precipitate and by adding again the racemic mixture, always in the same amount of the precipitated enantiomer. The cycle may be so repeated for an indefinite number of times.

For a general treatment of the spontaneous resolutions the following text is pointed out to which reference is made for the matter not specified in detail: J. Jaques, A. Collet, S. H. Wilen, "Enantiomers, Racemates and Resolution", J. Wiley & Son, New York, 1981.

The above described method, repeated at continuous cycle, allows the separation of the enantiomer esters of 2-hydroxy-3-(2-aminophenylthio)-3-(4-methoxyphenyl)propionic acid with practically quantitative yields and high optical purity, suitable for obtaining Diltiazem with the desired purity.

If necessary, the precipitate enantiomer may be further purified by crystallization. The mother liquors, containing substantially a racemic mixture, are re-used in the process of spontaneous resolution.

The compound of formula III in optical pure form is then cyclized directly or after hydrolysis to give the cyclic intermediate of formula V from which Diltiazem is obtained by alkylation and acetylation.

The spontaneous resolution process object of the present invention allows to obtain the (2S,3S) enantiomer of the compound of formula III with high optical purity and high productivity. Moreover the process object of the present invention results to be particularly advantageous for its simple industrial applicability and its thriftiness.

A further advantage consists in the fact that the resolution (spontaneous and therefore without the use of optical active bases) is carried out on an earlier, and therefore of less added value, intermediate of the synthesis. With the aim to better illustrate the present invention the following examples are given.

EXAMPLE 1

Threo-2-hydroxy-3-(2-aminophenylthio)-3-(4-methoxyphenyl)propionic acid methyl ester (10 g; 0.03 mols, (2R,3R):(2S,3S)=5.5:4.5), glacial acetic acid (35 ml) and isopropanol (100 ml) were put in a flask equipped with stirrer, thermometer and refrigerator. The mixture was heated to 40°-45° C. up to complete solution and then cooled at 34° C. in 15 minutes.

(2R,3R)-2-hydroxy-3-(2-aminophenylthio)-3-(4-methoxyphenyl)propionic acid methyl ester (50 mg; 0.15 mmols) was added at this temperature.

After cooling at 24° C. in one hour, this temperature was kept for a further hour under slow stirring. The precipitate was filtered and washed with isopropanol (20 ml) to give 2-hydroxy-3-(2-aminophenylthio)-3-(4-methoxyphenyl)propionic acid methyl ester (1.82 g) with $[\alpha]_D^{20} = -95.8°$ (c=0.5% CHCl$_3$; (2R,3R):(2S,3S)=97:3).

The washing liquors were evaporated to dryness and the solid residue (about 300 mg) was added to the mother liquors.

The racemic threo-2-hydroxy-3-(2-aminophenylthio)-3-(4-methoxyphenyl)propionic acid methyl ester (2.00 g; 0.006 mols) was added to the mother liquors and the procedure was repeated by seeding with (2S,3S)-2-hydroxy-3-(2-aminophenylthio)-3-(4-methoxyphenyl)-propionic acid methyl ester (50 mg; 0.15 mmols).

From the second cycle 2-hydroxy-3-(2-aminophenylthio)-3-(4-methoxyphenyl)-propionic acid methyl ester (1.85 g) was obtained with $[\alpha]_D^{20} = +66.0°$ (c=0.5% CHCl$_3$; (2S,3S):(2R,3R)=83:17).

For the third cycle the racemic threo-2-hydroxy-3-(2-aminophenylthio)-3-(4-methoxyphenyl)propionic acid methyl ester (1.1 g; 0.0033 mols) and (2R,3R)-2-hydroxy-3-(2-aminophenylthio)-3-(4-methoxyphenyl)-propionic acid methyl ester (0.47 g; 0.0014 mols) were added, by seeding with the optically pure (2R,3R) enantiomer (50 mg; 0.15 mmols).

2-Hydroxy-3-(2-aminophenylthio)-3-(4-methoxyphenyl)propionic acid methyl ester (1.77 g) was thus obtained with $[\alpha]_D^{20} = -85.8°$ (c=0.5% CHCl$_3$; (2R,3R):(2S,3S)=93:7).

The fourth cycle was carried out by adding, just like in the second cycle, the racemic methyl ester (2.00 g; 0.006 mols) and by seeding with the optical pure (2S,3S) enantiomer (100 mg; 0.30 mmols).

2-Hydroxy-3-(2-aminophenylthio)-3-(4-methoxyphenyl)propionic acid methyl ester (2.32 g) was obtained with $[\alpha]_D^{20} = +36.5°$ (c=0.5% CHCl$_3$; (2S,3S):(2R,3R)=68:32).

The mother liquors were poured under stirring into NaHCO$_3$ 8% solution (250 ml) and extracted twice with CH$_2$Cl$_2$ (100 ml+50 ml). The collected organic phases were washed with water (100 ml+50 ml).

After drying on Na$_2$SO$_4$, the organic phase was filtered and evaporated to dryness to give the threo-2-hydroxy-3-(2-aminophenylthio)-3-(4-methoxyphenyl)-propionic acid methyl ester (8.26 g) with 97.2% HPLC titre.

The charged product was recovered for a total of 99.8% (15.79 g; 100% HPLC titre).

EXAMPLE 2

Threo-2-hydroxy-3-(2-aminophenylthio)-3-(4-methoxyphenyl)propionic acid methyl ester (12.3375 kg; 37.00 mols, (2S,3S):(2R,3R)=52.4:47.6), toluene (35.24 l) and dimethylformamide (5.09 l) were charged into a 60 l reactor.

The mixture was heated to 43°-45° C. up to complete solution and then cooled at 20° C.

(2S,3S)-2-hydroxy-3-(2-aminophenylthio)-3-(4-methoxyphenyl)propionic acid methyl ester (5.8 g; 0.0174 mols) was added at this temperature as seed.

The cooling was continued up to the temperature of 15° C. in 30-35 minutes and the so obtained precipitate was filtered (see the table) washed with a mixture of toluene:dimethylformamide=87:13 (0.89 l), which was collected and added to the mother liquors, and then with toluene (0.78 l).

An amount, equal to the amount of the filtered precipitate, of racemic threo-2-hydroxy-3-(2-aminophenylthio)-3-(4-methoxyphenyl)propionic acid methyl ester was added and the volume (50 l) was restored with a mixture of toluene:dimethylformamide.

The mixture was heated at 43°-45° C. up to complete solution, then cooled at 20° C. and seeded with (2R,3R)-2-hydroxy-3-(2-aminophenylthio)-3-(4-methoxyphenyl)propionic acid methyl ester (5.8 g; 0.0174 mols) and the procedure of the first cycle was repeated. The cycle was repeated for 11 times in all and the obtained data are reported in the following table.

TABLE

| Cycle No. | Precipitated amount of (2S,3S) enantiomer | Precipitated amount of (2R,3R) enantiomer | $\alpha_D^{23}$ (a) | Optical purity |
|---|---|---|---|---|
| 1 | 1.22 kg | | +274.0° | 92.7% |
| 2 | | 1.268 kg | −289.9° | 97.7% |
| 3 | 1.288 kg | | +287.2° | 97.1% |
| 4 | | 1.283 kg | −278.6° | 94.2% |
| 5 | 1.294 kg | | +288.6° | 97.6% |
| 6 | | 1.331 kg | −288.0° | 97.4% |
| 7 | 1.429 kg | | +284.1° | 96.0% |
| 8 | | 1.406 kg | −287.6° | 97.3% |
| 9 | 1.355 kg | | +287.2° | 97.1% |
| 10 | | 1.355 kg | −289.2° | 97.8% |
| 11 | 1.245 kg | | +285.8° | 96.7% |

(a): The value was determined by dissolving 0.175 g of the product in 50 ml of methanol.

Maximum specific rotatory of the samples of the two pure enantiomers crystallized several times: +295.5 and −295.5 in the same conditions.

We claim:

1. A process for resolution of threo-2-hydroxy-3-(2-aminophenylthio)-3-(4-methoxyphenyl)propionic acid lower alkyl esters comprising creating a supersaturated solution of a mixture of the two enantiomers (2R,3R) and (2S,3S), wherein one prevails over the other, in a polar inert solvent or in a mixture of solvents wherein at least one of them is polar and wherein the racemate is soluble, bringing about a spontaneous crystallization of one of the two enantiomers from the solution, and recovering the thus-crystallized enantiomer.

2. A process according to claim 1 wherein the enantiomer mixture is dissolved at 40°-50° C. in the selected solvent and then cooled at a temperature lower than 35° C., the crystallization of the prevailing enantiomer is seeded by adding a small amount of the same, the precipitate is separated by filtration and the supersaturated conditions are restored by adding the racemate, and the cycle is repeated.

3. A process according to claim 1 or 2 wherein the solvent is selected from alcohols, weak organic acids and dipolar aprotic solvents or in admixture with a polar solvent.

4. A process according to claim 1 or 2 wherein the lower alkyl ester is the methyl ester.

* * * * *